United States Patent
Kondo

(10) Patent No.: US 8,201,453 B2
(45) Date of Patent: Jun. 19, 2012

(54) MEDIUM FATIGUE DETECTION APPARATUS AND MEDIUM FATIGUE DETECTION METHOD

(75) Inventor: Chikashi Kondo, Kanazawa (JP)

(73) Assignee: Murata Manufacturing Co., Ltd. (JP)

( * ) Notice: Subject to any disclaimer, the term of this patent is extended or adjusted under 35 U.S.C. 154(b) by 0 days.

(21) Appl. No.: 12/465,881

(22) Filed: May 14, 2009

(65) Prior Publication Data

US 2009/0223295 A1    Sep. 10, 2009

Related U.S. Application Data

(63) Continuation of application No. PCT/JP2008/052844, filed on Feb. 20, 2008.

(30) Foreign Application Priority Data

Feb. 28, 2007  (JP) .................. 2007-049549

(51) Int. Cl.
   *G01N 29/11* (2006.01)
(52) U.S. Cl. ........................... 73/600; 73/646
(58) Field of Classification Search .......... 73/159, 73/599, 600, 618, 646, 104, 105
   See application file for complete search history.

(56) References Cited

U.S. PATENT DOCUMENTS

| | | | | |
|---|---|---|---|---|
| 4,446,735 A * | 5/1984 | Weilacher | | 73/597 |
| 4,519,249 A | 5/1985 | Hunt | | |
| 4,603,584 A * | 8/1986 | Bartle et al. | | 73/599 |
| 4,607,341 A * | 8/1986 | Monchalin | | 702/136 |
| 4,612,807 A * | 9/1986 | Wunderer | | 73/580 |
| 5,661,243 A * | 8/1997 | Bryan et al. | | 73/632 |
| 5,922,960 A * | 7/1999 | Toda | | 73/597 |
| 6,212,130 B1* | 4/2001 | Brazeal et al. | | 367/93 |
| 6,407,964 B1* | 6/2002 | Hornung et al. | | 367/138 |
| 2002/0014120 A1* | 2/2002 | Wunderer et al. | | 73/597 |
| 2002/0079644 A1* | 6/2002 | Phinney | | 271/258.01 |
| 2003/0183012 A1* | 10/2003 | Wunderer et al. | | 73/602 |
| 2005/0189707 A1* | 9/2005 | Sano et al. | | 271/242 |

FOREIGN PATENT DOCUMENTS

EP     0 098 115 A1    1/1984

(Continued)

OTHER PUBLICATIONS

Chinese Office Action dated Sep. 16, 2010; Application No. 200880001248.2 with partial translation.

(Continued)

*Primary Examiner* — Hezron E Williams
*Assistant Examiner* — Rose M Miller
(74) *Attorney, Agent, or Firm* — Studebaker & Brackett PC; Tim L. Brackett, Jr.; John F. Guay

(57) ABSTRACT

A medium fatigue detection apparatus and a medium fatigue detection method detect fatigue of a sheet-like medium. The apparatus includes an ultrasonic sending device for oscillating ultrasonic waves as burst waves, an ultrasonic receiving device, and a sensed intensity detector. The ultrasonic sending device and ultrasonic receiving device are arranged to oppose each other and allow a sheet-like medium to pass between them. The ultrasonic waves sent from the ultrasonic sending device are incident on a principal surface of the sheet-like medium at a predetermined incident angle θ. Fatigue of the medium is detected by measuring a variation in sensed intensity of the ultrasonic waves having passed through the sheet-like medium.

12 Claims, 4 Drawing Sheets

FOREIGN PATENT DOCUMENTS

| | | |
|---|---|---|
| JP | 59-86531 | 5/1984 |
| JP | 3-54409 | 3/1991 |
| JP | 05-62192 | 3/1993 |
| JP | 05-097284 A | 4/1993 |
| JP | 2002-525627 | 8/2002 |
| JP | 2005-244425 A | 9/2005 |
| JP | 2006-250869 | 9/2006 |
| WO | 2007/017663 A1 | 2/2007 |

OTHER PUBLICATIONS

The Second Office Action from State Intellectual Property Office of People's Republic of China dated Mar. 29, 2011; Chinese Patent Application No. 200880001248.2 with translation.

The Extended European Search Report dated Feb. 17, 2012; EP Application No./Patent No. 08711650.5-1229/2128608 PCT/JP2008052844.

First examination results from Korean Intellectual Property Office, issued on Mar. 22, 2011; Korean Application No. 10-2009-7011095; and English language summary.

Second examination results from Korean Intellectual Property Office, issued on Sep. 26, 2011; Korean Application No. 10-2009-7011095; and English language summary.

* cited by examiner

NEW BANKNOTE

LOW FATIGUE LEVEL

HIGH FATIGUE LEVEL

MEDIUM FATIGUE DETECTION APPARATUS AND MEDIUM FATIGUE DETECTION METHOD

CROSS REFERENCE TO RELATED APPLICATIONS

The present application is a continuation of International Application No. PCT/JP2008/052844, filed Feb. 20, 2008, which claims priority to Japanese Patent Application No. JP 2007-049549, filed Feb. 28, 2007, the entire contents of each of these applications being incorporated herein by reference in their entirety.

BACKGROUND

1. Technical Field

The present invention relates to an apparatus and a method for detecting wrinkles, twists, tears, etc. of banknotes (bills), sheets of copy paper, plastic sheets, and so on.

2. Description of the Related Art

At the present time, ATMs (Automatic Telling Machines) are widely employed over the world. ATMs often handle fatigued banknotes (having wrinkles, twists, tears, etc.). In such a case, when the banknotes are taken into the ATM and are sorted based on different sorts of the banknotes by a sorting and handling mechanism installed in the ATM, there is a risk that the fatigued banknotes may jam inside the machine. To overcome the jamming problem of fatigued banknotes, highly fatigued banknotes are prevented from going back to the market. For example, banknote counters and ATMs at banks can be provided with a function of detecting and indentifying highly fatigued banknotes.

An example of a known system for detecting fatigue of a banknote etc. is described in Japanese Unexamined Patent Application Publication No. 5-97284 ("the '284 application"). In this detection system, an ultrasonic sending sensor and an ultrasonic receiving sensor are provided on the principal surface side of a medium to measure ultrasonic waves reflected by the medium. A surface condition (e.g., wrinkles) of the medium is detected by comparing the medium with previously input information about the distance between the medium and the sensor.

However, detection system described in the '869 application has problems because information about the distance between the medium and the sensor must be input in advance, and processing operations are complicated. Further, if the medium's position deviates from its expected position, for example, it becomes difficult to accurately measure the distance between the medium and the sensor.

In another example, Japanese Unexamined Patent Application Publication No. 2006-250869 ("the '869 application") describes a detection apparatus in which a banknote is guided to pass between an ultrasonic sending unit and an ultrasonic receiving unit. The banknote resonates upon irradiation of ultrasonic waves by the ultrasonic sending unit, and secondary radiation waves are received to determine a natural frequency of the banknote from the resonance frequency. The determined natural frequency is compared with the natural frequency of a normal banknote to recognize deterioration in rigidity of the banknote.

However, the detection apparatus described in the '869 application also has problems. The natural frequency of a normal banknote must be input in advance. In order to inspect plural kinds of banknotes by a single apparatus, therefore, plural types of data must be input to execute comparative processing operations for each type. Thus, versatility of the apparatus described in the '869 application is insufficient.

SUMMARY

To overcome the problems described above, embodiments in accordance with the invention provide a medium fatigue detection apparatus and a medium fatigue detection method, which have versatility and which can simply detect fatigue of a sheet-like medium with no necessity of previously inputting master data as a reference and executing comparative processing operations with respect to detected data.

An apparatus for detecting fatigue of a sheet-like medium by using ultrasonic waves according to an embodiment includes an ultrasonic sending means for oscillating the ultrasonic waves as burst waves, an ultrasonic receiving means, and a sensed intensity detecting means for detecting intensity of the ultrasonic waves sensed by the ultrasonic receiving means. The ultrasonic sending means and the ultrasonic receiving means are arranged to oppose each other with the sheet-like medium provided between the ultrasonic sending means and the ultrasonic receiving means. The ultrasonic waves sent from the ultrasonic sending means are incident on a principal surface of the sheet-like medium at a predetermined angle.

A detection method for detecting fatigue of a sheet-like medium according to an embodiment includes conveying the sheet-like medium to pass between an ultrasonic sending device and an ultrasonic receiving device, sending ultrasonic waves from the ultrasonic sending device to pass through the sheet-like medium, and receiving the ultrasonic waves by the ultrasonic receiving device. The method includes oscillating the ultrasonic waves sent from the ultrasonic sending device, as burst waves, to be incident on a principal surface of the conveyed sheet-like medium at a predetermined angle, receiving the ultrasonic waves having passed through the sheet-like medium by the ultrasonic receiving device, which is provided opposite the ultrasonic sending device, and detecting fatigue of the sheet-like medium by measuring a variation in sensed intensity of the received ultrasonic waves.

An apparatus for detecting fatigue of a sheet-like medium by using ultrasonic waves according to an embodiment includes an ultrasonic sending device that oscillates the ultrasonic waves as burst waves, an ultrasonic receiving device, and a sensed intensity detector that detects intensity of the ultrasonic waves sensed by the ultrasonic receiving device. The ultrasonic sending device and the ultrasonic receiving device are arranged to oppose each other with the sheet-like medium provided between the ultrasonic sender and the ultrasonic receiver. The ultrasonic waves sent from the ultrasonic sending device are incident on a principal surface of the sheet-like medium at a predetermined angle.

In an aspect of the invention, a sheet-like medium is excited by the ultrasonic waves sent from the ultrasonic sender, and the ultrasonic waves having changed with vibration of the sheet-like medium are received by the ultrasonic receiver. An excitation state of the sheet-like medium differs between a not-fatigued portion and a fatigued portion (including wrinkles, twists, tears, etc.). In the fatigued portion, a variation in the output voltage, which represents the sensed intensity of the ultrasonic waves, is larger than that in the not-fatigued portion. A level of the fatigue of the sheet-like medium is detected based on the magnitude of the variation in the output voltage.

In an embodiment of the invention, the ultrasonic waves sent from the ultrasonic sender are incident on the principal surface of the sheet-like medium at an angle of 5° or more with respect to a direction normal to the principal surface.

In an embodiment, a center axis of the ultrasonic sender and a center axis of the ultrasonic receiver are arranged to lie on a linear line in an opposed relation.

According to embodiments of the invention, the fatigue of the sheet-like medium can be detected by receiving the ultrasonic waves which have passed through the sheet-like medium, and by measuring the variation in the output voltage, which represents the sensed intensity of the ultrasonic waves.

DETAILED DESCRIPTION

A medium fatigue detection apparatus and a medium fatigue detection method according to the exemplary embodiments will be described with reference to the accompanying drawings.

Figure 1:
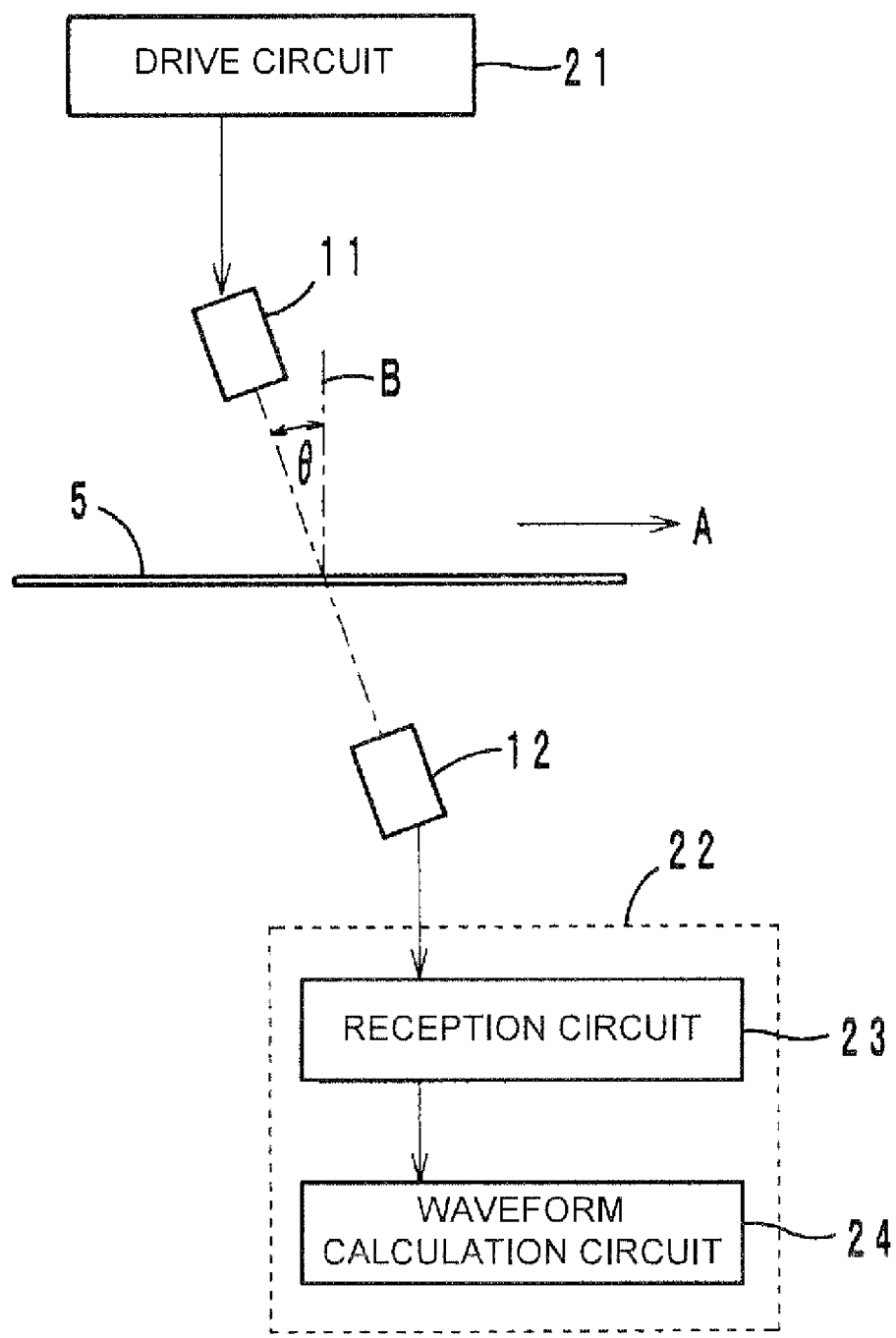
FIG. 1 is a side view of a medium fatigue detection apparatus according to an exemplary embodiment.

FIG. 1 illustrates an embodiment of a medium fatigue detection apparatus. The apparatus includes an ultrasonic sending device 11 coupled with a drive circuit 21, and an ultrasonic receiving device 12 coupled to a sensed intensity detector 22. The ultrasonic sending device 11 oscillates ultrasonic waves in the form of burst waves. The sensed intensity detector 22 includes a reception circuit 23 which includes an amplification circuit for amplifying received waves and a peak hold circuit, and a waveform calculation circuit 24.

As shown in FIG. 1, a sheet-like medium 5, i.e., a detection target, can be conveyed at a predetermined speed in the direction of arrow A between the ultrasonic sending device 11 and the ultrasonic receiving device 12. The sheet-like medium 5 can be provided as a paper medium, e.g., a banknote or a sheet of copy paper, a plastic sheet, or the like. The apparatus detects fatigue of the sheet-like medium 5, such as wrinkles, twists, tears etc.

The ultrasonic sending device 11 can be arranged to send ultrasonic waves that are incident on a principal surface of the sheet-like medium 5 at a predetermined incident angle θ with respect to a line B normal to the principal surface. Further, a center axis of the ultrasonic sending device 11 and a center axis of the ultrasonic receiving device 12 can lie on a linear line, and the sending device 11 and receiving device 12 can oppose one another about the sheet-like medium 5 that is conveyed between them. Such an arrangement increases utilization efficiency of the ultrasonic waves. The center axis of the ultrasonic sending device 11 and the center axis of the ultrasonic receiving device 12 can be slightly deviated to such an extent that the utilization efficiency of the ultrasonic waves would not be significantly reduced from a practical point of view.

The sheet-like medium 5 is excited upon irradiation of the ultrasonic waves from the ultrasonic sending device 11, and the ultrasonic waves having been changed with vibration of the sheet-like medium 5 are received by the ultrasonic receiving device 12. After the amplification circuit of the reception circuit 23 amplifies the received waves, which were provided in bursts at certain intervals, the peak hold circuit holds a maximum value of an output voltage generated upon receiving the ultrasonic waves. In such a state, a variation in the output voltage is measured by the waveform calculation circuit 24. An excitation state of the sheet-like medium 5 differs depending on the condition of the sheet-like medium 5 (i.e., between a fatigued portion including wrinkles, twists, tears, etc. and a non-fatigued portion). More specifically, in a fatigued portion, variation in the output voltage, which represents the sensed intensity of the ultrasonic waves, is larger than that in a non-fatigued portion (as described in detail later). A level of the fatigue of the sheet-like medium 5 can be detected based on the magnitude of the variation in the output voltage.

The magnitude of the variation in the output voltage differs depending on the fatigue condition of the sheet-like medium 5, e.g., a banknote, because a transmissive or reflective state of the ultrasonic waves varies corresponding to a degree of ruggedness on the surface of the medium 5. With such a variation in the transmissive or reflective state, the transmitted or reflected ultrasonic waves cause interference, thus giving rise to changes in the sensed intensity.

Figure 2A:
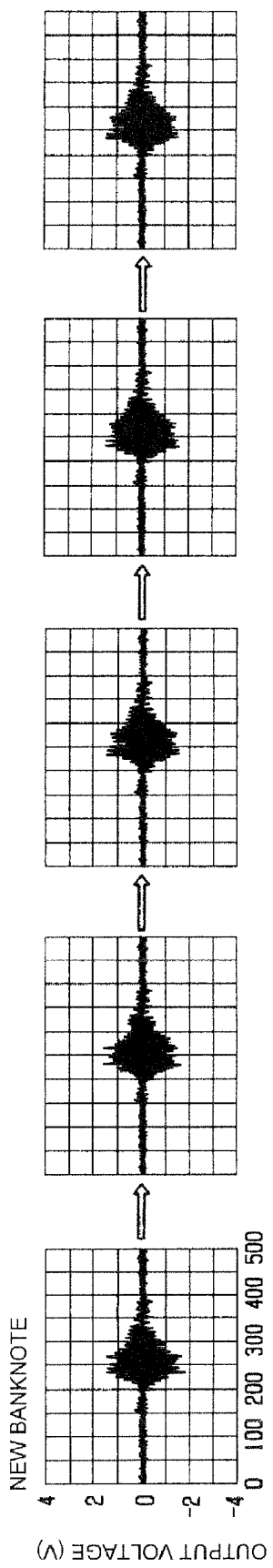
FIGS. 2A to 2C are graphs showing an example of output voltage that represents sensed intensity of ultrasonic waves having passed through a sheet-like medium.
Figure 2B:
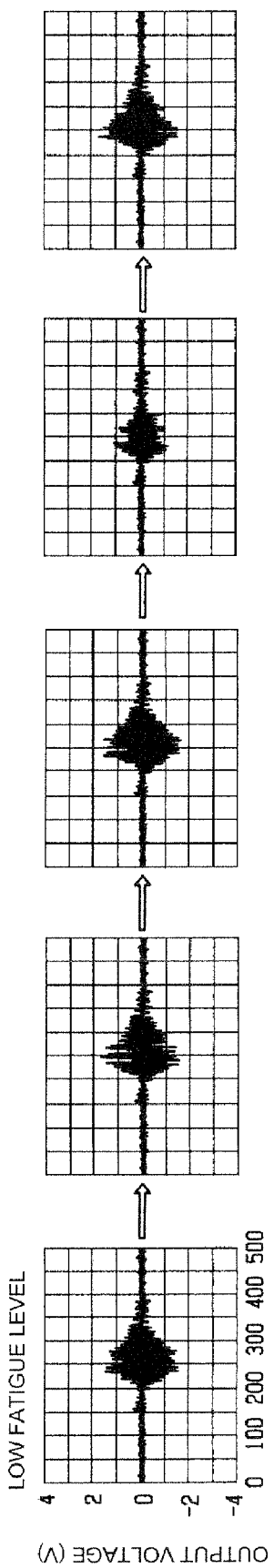
Figure 2C:
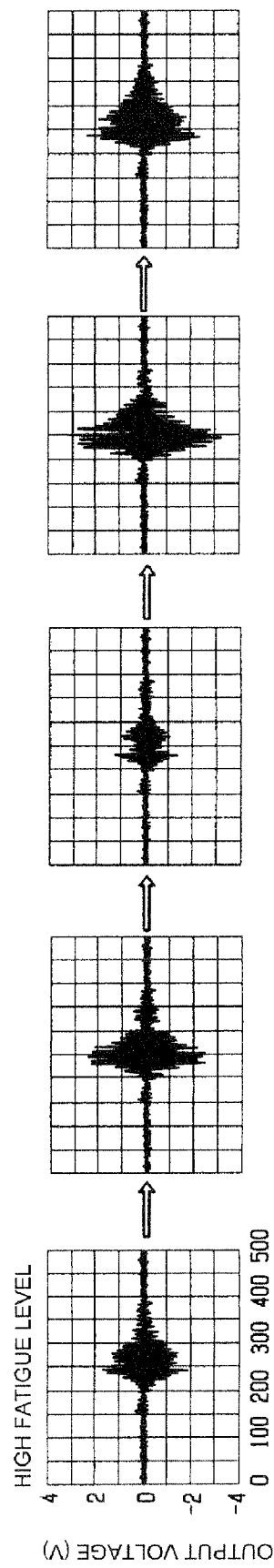

FIGS. 2A-2C show waveforms representing the sensed intensity of the ultrasonic waves, which have been received by the ultrasonic receiving device 12 and amplified by the reception circuit 23. In measuring the waveform, a banknote is used as the sheet-like medium 5, and the sheet-like medium 5 is conveyed at a predetermined speed. The sheet-like medium 5 is stopped whenever it is conveyed through 5 mm. In a stopped state, 10 pulses of 300-kHz ultrasonic waves are sent as burst waves from the ultrasonic sending device 11 and are received by the ultrasonic receiving device 12 after passing through the sheet-like medium 5. The spacing between the ultrasonic sending device 11 and the ultrasonic receiving device 12 is 20 mm, and the incident angle θ is 15°.

FIG. 2A shows a waveform of the output voltage representing the sensed intensity of the ultrasonic waves when the banknote is new. FIG. 2B shows a waveform of the output voltage representing the sensed intensity when the banknote has a low fatigue level. FIG. 2C shows a waveform of the output voltage representing the sensed intensity when the banknote has a high fatigue level.

Figure 3A:
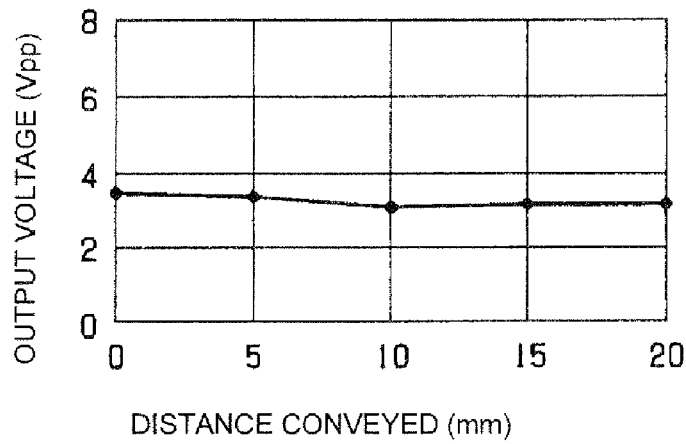
FIGS. 3A to 3C are graphs showing changes in the sensed intensity based on the output voltage shown in FIGS. 2A to 2C.
Figure 3B:
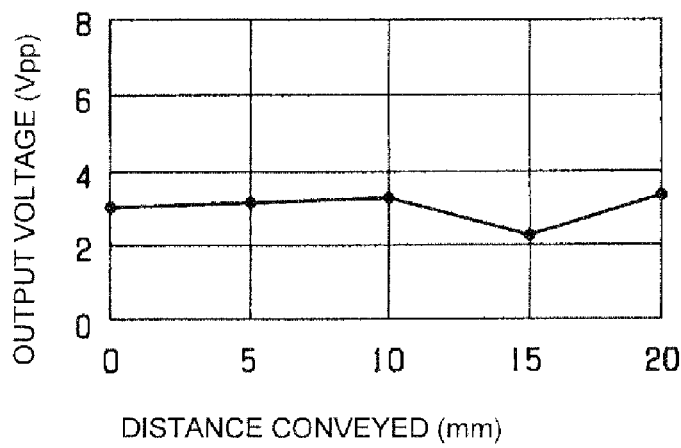
Figure 3C:
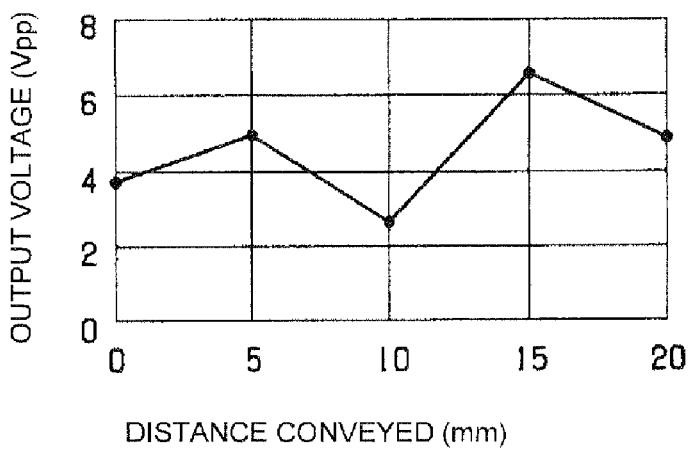

FIGS. 3A-3C is a graph showing a waveform representing a peak value (Vpp) of the output voltage shown in FIGS. 2A-2C, respectively. More specifically, FIG. 3A shows changes in the peak value (Vpp) of the output voltage representing the sensed intensity when the banknote is new. FIG. 3B shows similar changes when the banknote has a low fatigue level. FIG. 3C shows similar changes when the banknote has a high fatigue level.

As seen from FIGS. 2A to 3C, a variation in the sensed intensity (peak value) increases as the fatigue level increases. By measuring the variation in the sensed intensity, therefore, the fatigue of a sheet-like medium 5 (e.g., a banknote) can be easily detected without previously inputting master data as a reference and executing comparative processing operations with respect to detected data.

Figure 4A:
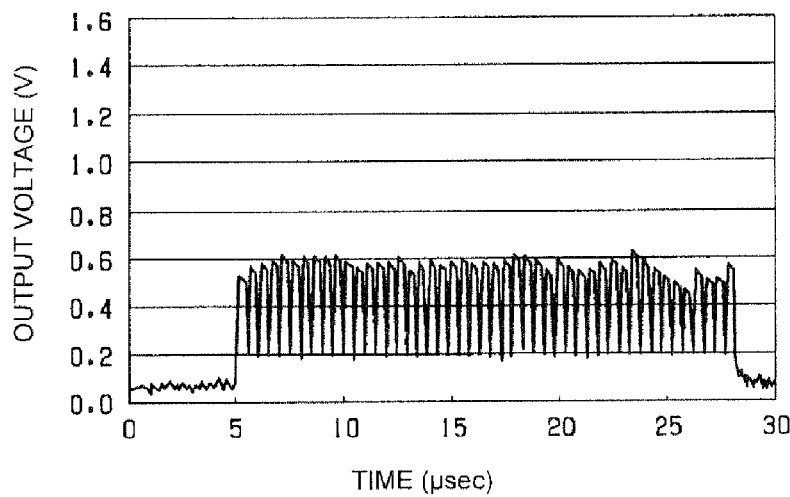
FIGS. 4A to 4C are graphs showing, in more detail, exemplary output voltages that represent sensed intensities of the ultrasonic waves for a new banknote and a fatigued banknote.
Figure 4B:
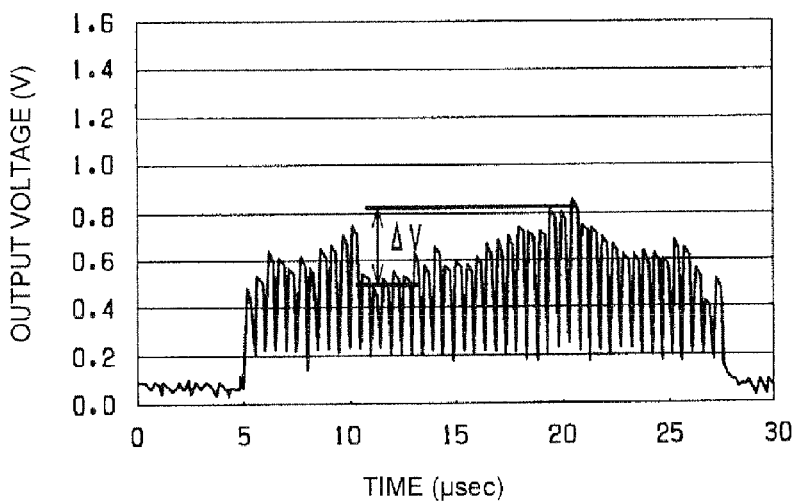
Figure 4C:
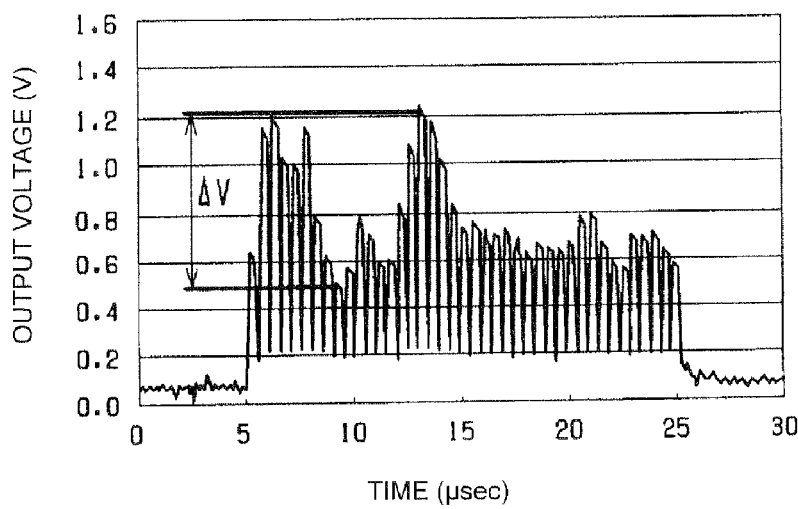

FIGS. 4A-4C show, in more detail, waveforms of the output voltage representing the sensed intensity of the ultrasonic waves when a peak of the output voltage on the (+) side is held. The waveform is measured by providing a spacing of 20 mm between the ultrasonic sending device 11 and the ultrasonic receiving device 12, setting the incident angle θ to 15°, conveying the sheet-like medium 5 at a speed of 1.0 m/sec, and applying 10 pulses of 300-kHz ultrasonic waves in the form of burst waves at intervals of 0.5 msec.

FIG. 4A shows a waveform of the output voltage representing the sensed intensity when the banknote is new. FIG. 4B shows a waveform of the output voltage representing the sensed intensity for a fatigued portion of the banknote that has a low fatigue level. FIG. 4C shows a waveform of the output voltage representing the sensed intensity for a fatigued portion of the banknote that has a high fatigue level. As seen from FIG. 4A, the output voltage hardly varies in the case of the new banknote. Also, as seen from FIG. 4B, when the banknote has a low fatigue level, a voltage difference ΔV between a maximum value and a minimum value of the output voltage is about 0.3 V. Namely, the variation in the output voltage is small. On the other hand, as seen from FIG. 4C, when the banknote has a high fatigue level, a voltage difference ΔV between a maximum value and a minimum value of the output voltage is about 0.7 V or more. Namely, the variation in the output voltage is extremely large. It is to be understood that, because the magnitude of the variation in the output voltage differs depending on, e.g., materials of the sheet-like medium 5, the voltage differences are not limited to the above-mentioned numerical values.

The incident angle θ will be described below. The incident angle θ is defined as an angle formed between the direction B normal to the principal surface of the sheet-like medium 5 and the direction in which the ultrasonic waves are sent from the ultrasonic sending device 11. Table 1, below, shows the output voltage (Vpp) measured by using the apparatus, which is used to measure the waveform of the output voltage representing the sensed intensity shown in FIG. 4, while the incident angle θ is changed in units of 5° in the range of 0° to 20°.

TABLE 1

| Incident Angle θ (°) | Output Voltage (Vpp) |
|---|---|
| 0 | immeasurable |
| 5 | 3.33 |
| 10 | 3.18 |
| 15 | 3.12 |
| 20 | 3.15 |

If the incident angle θ is smaller than 5°, this means that the ultrasonic waves are incident on the sheet-like medium 5 substantially at a right angle. In some cases, therefore, the incident ultrasonic waves are multi-reflected and the variation in the output voltage representing the sensed intensity is increased to such an extent as making the fatigue of the sheet-like medium 5 undetectable. As shown in Table 1, a practically usable output voltage can be obtained at the incident angle of 5° or more. When the incident angle is in the range of 10° to 20°, the output voltage can be obtained at a satisfactory level sufficient to exclude the influence of driving noise. Even when the incident angle exceeds 20°, the measurement of output voltage is practically possible.

However, when determining a distance between the ultrasonic sending device 11 and the ultrasonic receiving device 12, consideration should be given as to whether the distance is so large that it would undesirably reduces sensitivity and enlarges the apparatus size. Further, because each of the ultrasonic sending device 11 and the ultrasonic receiving device 12 has a predetermined thickness, the ultrasonic sending device 11 and the ultrasonic receiving device 12 may contact the sheet-like medium 5 being conveyed if the incident angle θ is set too large. In consideration of those points, an upper limit value of the incident angle θ is preferably not larger than 20°.

Further, the distance between the ultrasonic sending device 11 and the ultrasonic receiving device 12 is preferably 20 mm or more. The reason is as follows. When the ultrasonic sending device 11 is driven, driving noise is generated. A predetermined distance is desirably left between the sheet-like medium 5 and each of the devices 11, 12 in order to sufficiently separate the driving noise from the output voltage representing the sensed intensity of the ultrasonic waves, which can be obtained from the fatigued portion of the sheet-like medium 5.

Also, the sheet-like medium 5 can be conveyed to pass a middle point between the devices 11 and 12 although the sheet-like medium 5 can be conveyed to pass between the devices 11 and 12 at another point such as a point biased to either side.

Additionally, the devices 11 and 12 can be arranged in a positional relationship that is reversed to that illustrated in FIG. 1, and the sheet-like medium 5 may be conveyed in a direction opposed to the direction of arrow A.

To increase sensitivity, each of the ultrasonic sending device 11 and the ultrasonic receiving device 12 preferably has narrow directivity. Narrower directivity is effective in detecting the fatigued portion of the sheet-like medium 5 in a narrower range and increasing the sensed intensity of the ultrasonic waves.

With the embodiment described above, the ultrasonic waves are oscillated as burst waves from the sending device 11. By oscillating the ultrasonic waves in the form of burst waves, the sent waves can be specified per pulse and interference waves generated upon transmissive or reflective behaviors of the sent waves can be detected by the receiving device 12. Therefore, embodiments not only detect the presence or the absence of fatigue of the sheet-like medium 5, but also the fatigued position can be specified. If ultrasonic waves are generated in a form other than burst waves, for example, if the ultrasonic waves are oscillated as standing waves, the sheet-like medium 5 would be brought into a state where the oscillated ultrasonic waves are always irradiated to the sheet-like medium 5, and which one of the oscillated waves is reflected and causes interference could not be specified. Thus, the presence or the absence of the fatigued portion, including wrinkles, etc., cannot be determined and a difficulty arises in specifying the position of the fatigued portion.

As described above, the invention can be usefully practiced as an apparatus and a method for detecting fatigue of a medium, such as a banknote. For example, the present invention is advantageous in eliminating the necessity of previously inputting master data as a reference and executing comparative processing operations with respect to detected data, having versatility, and enabling fatigue of a sheet-like medium to be simply detected.

Although a limited number of embodiments are described herein, one of ordinary skill in the art will readily recognize that there could be variations to any of these embodiments and those variations would be within the scope of the appended claims. Thus, it will be apparent to those skilled in the art that various changes and modifications can be made to the medium fatigue detection apparatus and method described herein without departing from the scope of the appended claims and their equivalents.

What is claimed is:

1. A medium fatigue detection apparatus for detecting fatigue of a sheet medium by using fatigue-detecting ultrasonic waves, the medium fatigue detection apparatus comprising:
    ultrasonic sending means for oscillating fatigue-detecting ultrasonic waves as burst waves;

ultrasonic receiving means for sensing the burst waves;

sensed intensity detecting means for detecting intensity of the burst waves sensed by the ultrasonic receiving means; and fatigue detecting means for detecting fatigue of the sheet medium by measuring variation in the detected burst wave intensities and detecting fatigue based on a magnitude of the measured variation, wherein the ultrasonic sending means and the ultrasonic receiving means are provided to oppose each other such that fatigue-detecting ultrasonic waves sent from the ultrasonic sending device are incident at a predetermined angle on a principal surface of the sheet medium passing between the ultrasonic sending device and the ultrasonic receiving device.

2. The medium fatigue detection apparatus according to claim 1, wherein a center axis of the ultrasonic sending means and a center axis of the ultrasonic receiving means are arranged to lie on a same linear line.

3. The medium fatigue detection apparatus according to claim 1, wherein the burst waves sent from the ultrasonic sending device are incident on the principal surface of the sheet medium at an angle in the range of 5° to 20° with respect to a direction normal to the principal surface.

4. The medium fatigue detection apparatus of claim 1, wherein said burst waves are applied in predetermined spatial intervals on the sheet medium, and said variation in the sensed intensities is measured in the predetermined spatial intervals.

5. A medium fatigue detection method for detecting fatigue of a sheet medium by conveying the sheet medium to pass between ultrasonic sending device and ultrasonic receiving device, sending fatigue-detecting ultrasonic waves from the ultrasonic sending device to pass through the sheet medium, and receiving the fatigue- detecting ultrasonic waves by the ultrasonic receiving device, the medium fatigue detection method comprising:

oscillating the fatigue-detecting ultrasonic waves sent from the ultrasonic sending device, as burst waves, to be incident on a principal surface of the conveyed sheet medium at a predetermined angle;

receiving the fatigue-detecting ultrasonic burst waves having passed through the sheet medium by the ultrasonic receiving device, which is provided to oppose the ultrasonic sending means;

sensing intensity of the received fatigue-detecting ultrasonic burst waves; and detecting fatigue of the sheet medium by measuring variation in the sensed intensities of the received burst waves and detecting fatigue based on a magnitude of the measured variation.

6. The medium fatigue detection method according to claim 5, wherein the ultrasonic sending device and the ultrasonic receiving device are arranged to lie on a same linear line.

7. The medium fatigue detection method according to claim 5, wherein the burst waves sent from the ultrasonic sending device are incident on the principal surface of the sheet medium at an angle in the range of 5° to 20° with respect to a direction normal to the principal surface.

8. The medium fatigue detection method of claim 5, wherein oscillating the fatigue-detecting ultrasonic waves as burst waves is performed in predetermined spatial intervals on the sheet medium, and said variation in the sensed intensities is measured in the predetermined spatial intervals.

9. A medium fatigue detection apparatus for detecting fatigue of a sheet medium by using fatigue-detecting ultrasonic waves, comprising:

an ultrasonic sending device configured to oscillate fatigue-detecting ultrasonic waves as burst waves;

an ultrasonic receiving device configured to sense the burst waves;

a conveying device positioned between the ultrasonic sending device and the ultrasonic receiving device;

a sensed intensity detector that detects intensity of the burst waves sensed by the ultrasonic receiving device; and a fatigue detecting apparatus configured to detect fatigue of the sheet medium by measuring variation in the detected burst wave intensities and detecting the fatigue based on a magnitude of the measured variation, wherein the ultrasonic sending device and the ultrasonic receiving device are provided to oppose each other such that fatigue-detecting ultrasonic burst waves sent from the ultrasonic sending device are incident at a predetermined angle on a principal surface of the sheet medium passing between the ultrasonic sending device and the ultrasonic receiving device.

10. The medium fatigue detection apparatus according to claim 9, wherein a center axis of the ultrasonic sending device and a center axis of the ultrasonic receiving device are arranged to lie on a same linear line.

11. The medium fatigue detection apparatus according to claim 9, wherein the burst waves sent from the ultrasonic sending device are incident on the principal surface of the sheet medium at an angle in the range of 5° to 20° with respect to a direction normal to the principal surface.

12. The medium fatigue detection apparatus of claim 9, wherein said ultrasonic sending device is configured to oscillate said burst waves in predetermined spatial intervals, and said conveying device is configured to convey the sheet medium in the predetermined spatial intervals.

* * * * *